(12) United States Patent
Klettke et al.

(10) Patent No.: US 6,779,656 B2
(45) Date of Patent: Aug. 24, 2004

(54) POLYMERIZABLE PREPARATIONS BASED ON EPOXIDES THAT CONTAIN SILICON

(75) Inventors: Thomas Klettke, Hechendorf (DE); Wolfgang Weinmann, Gilching (DE)

(73) Assignee: 3M Espe AG, Seefeld (DE)

( * ) Notice: Subject to any disclaimer, the term of this patent is extended or adjusted under 35 U.S.C. 154(b) by 0 days.

(21) Appl. No.: 10/169,911

(22) PCT Filed: Jan. 15, 2001

(86) PCT No.: PCT/EP01/00388

§ 371 (c)(1),
(2), (4) Date: Jul. 11, 2002

(87) PCT Pub. No.: WO01/51540

PCT Pub. Date: Jul. 19, 2001

(65) Prior Publication Data

US 2003/0035899 A1 Feb. 20, 2003

(30) Foreign Application Priority Data

Jan. 13, 2000 (DE) .......................................... 100 01 228

(51) Int. Cl.⁷ ......................... B65D 25/08; C08L 63/00; C08K 3/34; C09J 163/00
(52) U.S. Cl. .................... 206/219; 206/524.1; 156/329; 156/330; 523/400; 523/435; 523/440; 523/443; 523/444; 525/523; 525/524; 525/525; 522/71; 522/77; 522/100
(58) Field of Search ................................. 428/413, 414, 428/415, 416, 417, 418, 446, 447, 448; 156/329, 330; 427/2.1, 2.26, 2.29, 386, 387; 523/400, 435, 440, 443, 444; 525/523, 524, 525, 474, 476; 206/219, 524.1; 522/71, 77

(56) References Cited

U.S. PATENT DOCUMENTS

| 5,639,413 | A |   | 6/1997 | Crivello |
| 5,863,970 | A | * | 1/1999 | Ghoshal et al. .............. 523/434 |
| 6,245,828 | B1 | * | 6/2001 | Weinmann et al. ......... 522/148 |

FOREIGN PATENT DOCUMENTS

| DE | 19648283 | 5/1998 |
| EP | 0897710 | 2/1999 |
| JP | 58168658 | 5/1983 |
| WO | 9833645 | 8/1998 |
| WO | 0019966 | 4/2000 |
| WO | 0019967 | 4/2000 |

* cited by examiner

*Primary Examiner*—Philip Tucker
*Assistant Examiner*—Michael Feely
(74) *Attorney, Agent, or Firm*—Crowell & Moring LLP

(57) ABSTRACT

The invention relates to polymerizable preparations which contain: (a) 3 to 80 wt. % of an epoxy or of a mixture of epoxies of general formula (I), whereby n and m, independent of one another, represent 0, 1, 2 or 3, and n+m ranges from 2 to 6, and whereby the molar mass of the epoxy or the average molar mass of the mixture of epoxies ranges from 250 to 1000 g/mol; (b) 0 to 80 wt. % of an epoxy or of a mixture of epoxies that differ from (a); (c) 3 to 85 wt. % of fillers; (d) 0.001 to 25 wt. % of initiators, retarders and/or accelerators, and; (e) 0 to 25 wt. % of auxiliary agents, whereby the specified percentages refer to the total weight of the preparation.

14 Claims, No Drawings

POLYMERIZABLE PREPARATIONS BASED ON EPOXIDES THAT CONTAIN SILICON

The invention relates to polymerizable preparations based on epoxides that contain silicon, and to their use.

In polymerizable dental compositions use has to date been made predominantly of methacrylate monomers and acrylate monomers. Particular attention is deserved by the 2,2-bis[4,1-phenyleneoxy(2-hydroxy-3,1-propane-diyl)methacrylate]-propylidene (bis-GMA) described by Bowen (U.S. Pat. No. 3,066,112). Mixtures of this methacrylate with triethylene glycol dimethacrylate are still used even today as a monomer matrix for dental plastic direct filling materials. Methacrylic derivatives of the diformylated bis (hydroxymethyl)tricyclo[5.2.1.0$^{2.6}$]-decane are also established as monomers for dental composites (W. Gruber et al., DE-A-27 14 538; W. Schmitt et al., DE-C-28 16 823; J. Reiners et al., EP-A-0 261 520). A great disadvantage of the known polymerizable dental compositions is the polymerization shrinkage, which in the case of filling material applications may, for example, give rise to secondary caries as a result of the formation of gaps at the edges. Furthermore, in the case of acrylate-based dental compositions, the inhibition polymerization by oxygen leads to the formation of what is known as a greasy layer, which in the case of fillings, for example, is unwanted and may even be harmful.

Despite the extensive experience which exists with epoxides and cycloaliphatic epoxides (U.S. Pat. No. 2,716,123, U.S. Pat. No. 2,750,395, U.S. Pat. No. 2,863,881, U.S. Pat. No. 3,187,018), such monomers and cationically polymerizable compositions formulated from them, having the properties needed for dental applications, have not become commercially available at any point in time.

The preparation of bifunctional cycloaliphatic epoxides has already been known for a good deal of time (U.S. Pat. No. 2,750,395, U.S. Pat. No. 900,506, U.S. Pat. No. 907,149, U.S. Pat. No. 2,745,847, U.S. Pat. No. 2,853,499, U.S. Pat. No. 3,187,018, U.S. Pat. No. 2,863,881, U.S. Pat. No. 2,853,498). Silicon-containing cycloaliphatic epoxides for producing three-dimensional objects by means of stereolithography were described by Crivello et al. in various publications (WO 96/30182, EP-A-0 449 027; J. Polym. Sci., Part A: Polym. Chem. 28 (1990) 479, ibid. 31 (1993) 2563; ibid. 31 (1993) 2729; ibid. 31 (1993) 3109; ibid. 31 (1993) 3121; ibid. 33 (1995) 2463).

The known cycloaliphatic epoxides essentially comprise low molecular weight monomers which, although possessing reduced polymerization shrinkage (DE-A-4 340 949), fail to meet the requirements imposed on materials for dental applications, owing to their toxicological properties.

Cationically curable epoxide compositions for dental applications are known, for example, from U.S. Pat. No. 5,556,896. That document describes epoxide compositions which have necessarily to contain spiroorthocarbonates as shrinkage compensating monomers.

Moreover, WO 95/30402 describes photopolymerizable compounds which comprise epoxide monomers. The compositions described therein are unsuitable for dental applications in the oral medium, owing to their high water absorption in the polymerized state.

The specifications WO 98/47046, WO 98/47047, and EP-A-0 897 710 describe epoxide compositions for dental applications that feature a novel initiator system but are based on conventional epoxide monomers. WO 98/22521 describes polymerizable compositions based on epoxides, intended for dental applications inter alia. Disadvantages of the epoxide compositions disclosed therein are the relatively high viscosity and the moderate reactivity of the monomer-containing compositions.

The epoxide compositions known to date, especially where monomers of low viscosity have been used, have exhibited high toxicity and/or mutagenicity and thereby restricting the possibilities for dental application.

An object of the present invention is to provide preparations which feature good handling properties, good processing properties, low volume shrinkage, and high reactivity on polymerization, and, in the polymerized state, high stability and good biocompatibility in the oral medium. Furthermore, the monomers are to exhibit low viscosity in combination with low toxicity and mutagenicity.

In accordance with the invention this object is achieved by means of polymerizable preparations containing
(a) from 3 to 80% by weight of an epoxide or of a mixture of epoxides of the general formula:

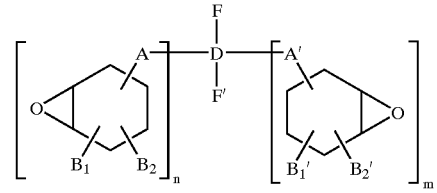

where
A and A' independently of one another are optional or represent an unbranched or branched aliphatic, cycloaliphatic or aromatic radical having from 1 to 13 carbon atoms or a combination of these radicals, it being possible for one or more carbon atoms to have been replaced by O, (C=O), O(C=O), Si, N, S, B1, B1', B2, and B2' independently of one another are H, an unbranched or branched aliphatic, cycloaliphatic or aromatic radical having from 1 to 6 carbon atoms or a combination of these radicals, it being possible for one or more carbon atoms to have been replaced by O, (C=O), O(C=O), Si, N, S, F and F' independently of one another are optional or represent an unbranched or branched aliphatic, cycloaliphatic or aromatic radical having from 1 to 10 carbons or a combination of these radicals, it being possible for one or more carbon atoms to have been replaced by O, (C=O), O(C=O), Si, N, S, D is an unbranched or branched aliphatic, cycloaliphatic or aromatic radical having from 1 to 15 carbon atoms or a combination of these radicals, it being possible for at least one carbon atom to have been replaced by SiGG', SiG or Si and for one or more carbon atoms to have been replaced by O, (C=O), O(C=O), N or S, G and G' independently of one another are H, an unbranched or branched aliphatic, cycloaliphatic or aromatic radical having from 1 to 8 carbon atoms or a combination of these radicals, it being possible for one or more carbon atoms to have been replaced by O, (C=O), O(C=O), Si, N, S, n and m independently of one another are 0, 1, 2 or 3 and n+m gives from 2 to 6 and where the molecular weight of the epoxide or the average molecular weight of the mixture of epoxides is from 250 to 1000 g/mol, (b) from 0 to 80% by weight of an epoxide or of a mixture of epoxides which are different than (a), (c) from 3 to 85% by weight of fillers,
(d) from 0.01 to 25% by weight of initiators, retardants and/or accelerators,
(e) from 0 to 25% by weight of auxiliaries, the percentages being based in each case on the total weight of the preparation.

Where A or A' being optional means that in their absence covalent bonds exist between adjacent atoms.

Preferred polymerizable preparations contain
(a) from 5 to 50% by weight of an epoxide or of a mixture of epoxides of the general formula:

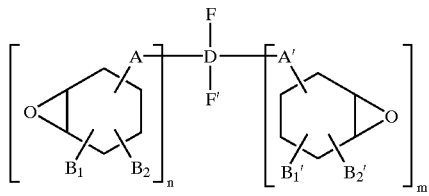

where
A and A' independently of one another are optional or represent an unbranched or branched aliphatic, cycloaliphatic or aromatic radical having from 1 to 10 carbon atoms or a combination of these radicals, it being possible for one or more carbon atoms to have been replaced by O, C=O, O(C=O), Si, B1, B1', B2, and B2' independently of one another are H, an unbranched or branched aliphatic radical having from 1 to 4 carbon atoms, it being possible for one or more carbon atoms to have been replaced by O, (C=O), O(C=O), Si, F and F' independently of one another are optional or represent an unbranched or branched aliphatic, cycloaliphatic or aromatic radical having from 1 to 10 carbons or a combination of these radicals, it being possible for one or more carbon atoms to have been replaced by O, (C=O), O(C=O), Si, N, S, D is an unbranched or branched aliphatic, cycloaliphatic or aromatic radical having from 1 to 15 carbon atoms or a combination of these radicals, it being possible for at least one carbon atom to have been replaced by SiGG', SiG or Si and for one or more carbon atoms to have been replaced by O, (C=O), O(C=O), G and G' independently of one another are H, an unbranched or branched aliphatic, cycloaliphatic or aromatic radical having from 1 to 8 carbon atoms or a combination of these radicals, it being possible for one or more carbon atoms to have been replaced by O, (C=O), O(C=O), Si, n and m independently of one another are 0, 1, 2 or 3 and n+m gives from 2 to 6
and where the molecular weight of the epoxide or the average molecular weight of the mixture of epoxides is from 250 to 1000 g/mol, (b) from 0 to 60% by weight of an epoxide or of a mixture of epoxides which are different than (a),
(c) from 15 to 85% by weight of fillers,
(d) from 0.01 to 20% by weight of initiators, retardants and/or accelerators,
(e) from 0 to 25% by weight of auxiliaries, the percentages being based in each case on the total weight of the preparation.

Among the epoxides of the components (a) particular preference is given to those comprising one of the following constituents D, in each case attached by the silicon atom to the constituents A and/or A':

i. Si
ii. SiG
iii. SiGG' iv. 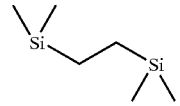

v. 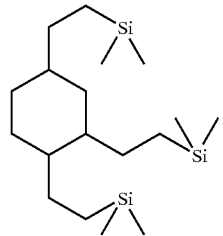

vi. 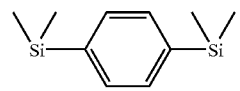

vii. 

where G and G' independently of one another are an unbranched or branched aliphatic, cycloaliphatic or aromatic radical having from 0 to 8 carbon atoms or a combination of these radicals, it being possible for one or more carbon atoms to have been replaced by O, (C=O), O(C=O), Si.

As a result of the use of epoxides or of an epoxide mixture according to component (a) having an average molecular weight of from 250 to 1000 g/mol, the preparations of the invention have better processing properties and better handling properties. This derives in particular from a low viscosity of the component (a) in the preparations of the invention. Particularly advantageous epoxides or an epoxide mixture according to component (a) are those having an average molecular weight of from 250 to 500 g/mol.

It has surprisingly been found that the mutagenicity of these low-viscosity epoxides or epoxide mixtures is low.

Suitable preparations may in particular comprise as component (a) one or more epoxides of the following formula:

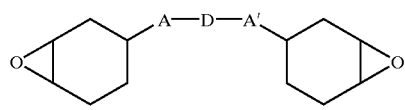

where
A and A' independently of one another are optional or represent an aliphatic radical having from 1 to 2 carbon atoms,
D is an unbranched or branched aliphatic, cycloaliphatic or aromatic radical having from 1 to 10 carbon atoms or a combination of these radicals, it being possible for at least one carbon atom to have been replaced by SiGG' and for one or more carbon atoms to have been replaced by O, (C=O), O(C=O), G and G' independently of one another are an unbranched or branched aliphatic or aromatic radical having from 1 to 8 carbon atoms or a combination of theses radicals, it being possible for one or more carbon atoms to have been replaced by O, (C=O), O(C=O), Si, and where the molecular weight of the epoxide or the average molecular weight of the mixture of epoxides is from 250 to 600 g/mol.

Surprisingly it has been found that the polymerizable preparation of the invention has particularly good biocompatibility properties when it comprises as component (a) one or more of the following epoxides:

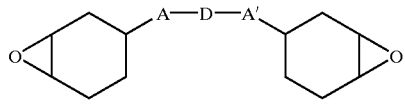

where
- A and A' independently of one another are optional or represent an aliphatic radical having from 1 to 2 carbon atoms,
- D is SiGG',
- G and G' independently of one another are an unbranched or branched aliphatic radical having from 1 to 8 carbon atoms or a combination of these radicals, and where the molecular weight of the epoxide or the average molecular weight of the mixture of epoxides is from 250 to 500 g/mol.

Particularly good results are the outcome of preparations comprising one or more of the following epoxides, named below in accordance with the valid IUPAC nomenclature:

i. methylbis[2-(7-oxabicyclo[4.1.0]hept-3-yl)ethyl] phenyl-silane (CAS No. 154265-59-5)

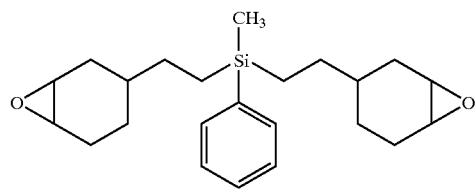

ii. dimethylbis[2-(7-oxabicyclo[4.1.0]hept-3-yl)methyl]-silane

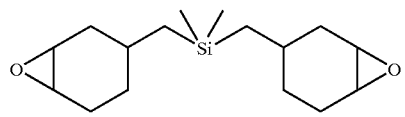

iii. dimethyl[2-(7-oxabicyclo[4.1.0]hept-3-yl)methyl][2-(7-oxabicyclo[4.1.0]hept-3-yl)ethyl]-silane

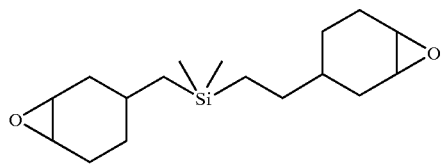

iv. 1,4-phenylenebis[dimethyl[2-(7-oxabicyclo-[4.1.0] hept-3-yl)ethyl]]-silane (CAS No. 20988-18-5)

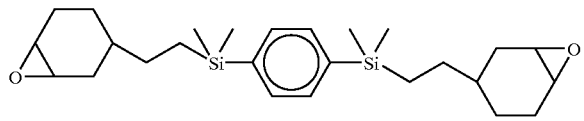

v. 1,2-ethylenebis[dimethyl[2-(7-oxabicyclo[4.1.0]hept-3-yl)ethyl]]-silane

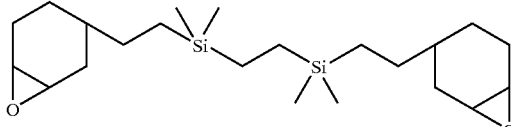

vi. dimethylbis[2-(7-oxabicyclo[4.1.0]hept-3-yl)ethyl]-silane

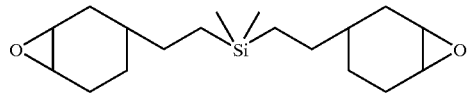

vii. 1,3-bis[2-(3,4-epoxycyclohexyl)ethyl]-1,1,3,3-tetramethyldisiloxane (CAS No. 18724-32-8)

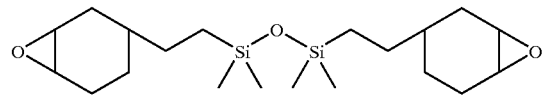

viii. 2,5-bicyclo[2.2.1]heptylenebis[dimethyl[2-(7-oxabicyclo[4.1.0]hept-3-yl)ethyl]]-silane

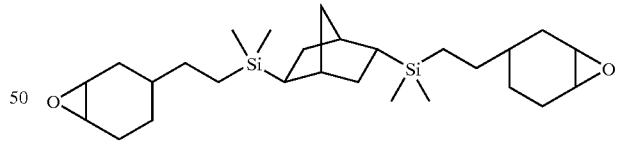

ix. 1,6-hexylenebis[dimethyl[2-(7-oxabicyclo-[4.1.0] hept-3-yl)ethyl]]-silane

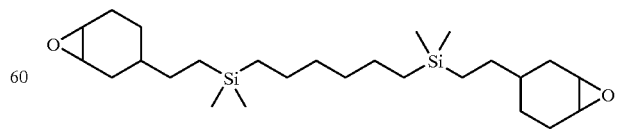

x. 1,1',1''-(1,2,4-cyclohexylenetris(dimethyl[2-(7-oxabicyclo[4.1.0]hept-3-yl)ethyl]))-silane

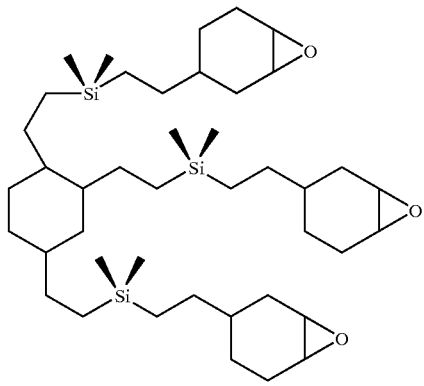

xi. 3-[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-3-phenyl-trisiloxane (CAS No. 90393-84-3)

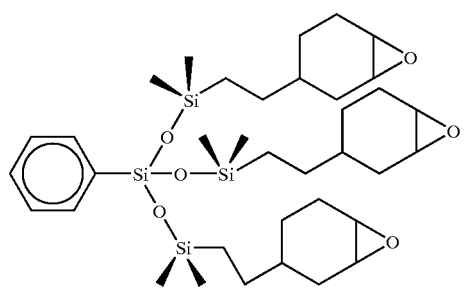

xii. 1,1',1''-(1,2,4-cyclohexanetriyltri-2,1-ethanediyl)tris[1,1,3,3-tetramethyl-3-[2-(7-oxabicyclo[4.1.0]hept-3-yl)ethyl]]-disiloxane (CAS No. 154265-70-0)

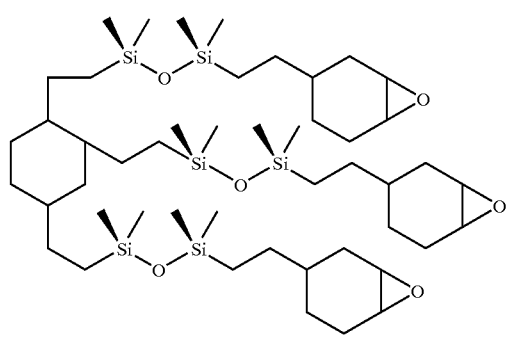

xiii. 3,3-bis[[dimethyl[2-(7-oxabicyclo[4.1.0]hept-3-yl)ethyl]silyl]oxy]-1,1,5,5-tetramethyl-1,5-bis[2-(7-oxabicyclo[4.1.0]hept-3-yl)ethyl]-trisiloxane (CAS No. 121239-70-1)

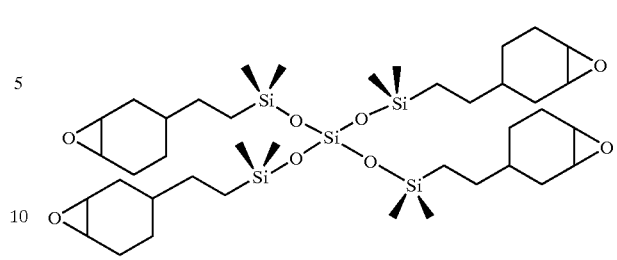

xiv. 3-[[dimethyl[2-(7-oxabicyclo[4.1.0]hept-3-yl)ethyl]silyl]oxy]-1,1,3,5,5-pentamethyl-1,5-bis[2-(7-oxabicyclo[4.1.0]hept-3-yl)ethyl]-trisiloxane (CAS No. 121239-71-2)

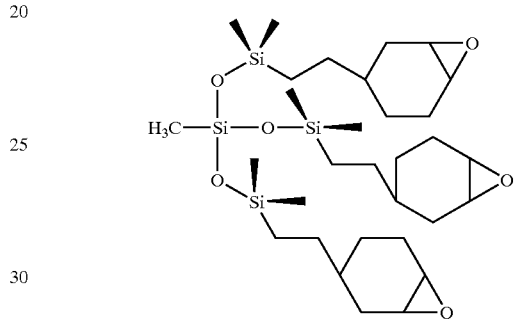

In addition to the silicon-containing epoxides described, the polymerizable preparations of the invention may comprise other epoxides as component (b). Epoxides according to (b) may, for example, be: 3,4-epoxycyclohexylmethyl 3,4-epoxycyclohexanecarboxylate (U.S. Pat. No. 2,716,123), 3,4-epoxy-6-methylcyclohexyl 3,4-epoxy-6-methylcyclohexanecarboxylate (U.S. Pat. No. 2,716,123) or related epoxides, vinylcyclohexene diepoxide (U.S. Pat. No. 2,948,688), dicyclopentadiene dioxide (U.S. Pat. No. 2,985,667), bis(3,4-epoxycyclohexylmethyl) adipate (U.S. Pat. No. 2,750,395, U.S. Pat. No. 2,863,881, U.S. Pat. No. 3,187,018), 7-oxabicyclo[4.1.0]heptane, 3,3',3'',3'''-[(2,4,6,8-tetramethylcyclotetrasiloxane-2,4,6,8-tetrayl)tetra-2,1-ethanediyl]tetrakis- of the following formula:

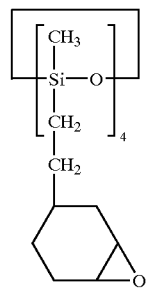

7-oxabicyclo[4.1.0]heptane, 3,3',3'',3''',3''''-[(2,4,6,8,10-pentamethylcyclopentasiloxane-2,4,6,8,10-pentayl)penta-2,1-ethanediyl]pentakis- of the following formula:

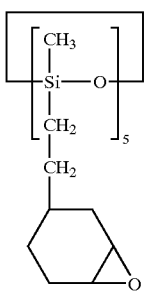

The epoxides of component (b) may be present in a concentration of from 0 to 80%, preferably from 0 to 60% by weight, based in each case on the total weight of the preparation.

Inorganic fillers according to component (c) may be customary dental fillers, examples being quartz, ground glasses which are optionally X-ray-opaque and are optionally reactive, fluorides of low solubility, such as $CaF_2$, $YF_3$ (EP-B-0 238 025), silica gels, and also pyrogenic silica and/or granules thereof.

Also present in component (c) as fluoride donor constituents, there may be one or more water-soluble inorganic complex fluoride of the general formula $A_nMF_m$, in which A is a monovalent or polyvalent cation, M is a metal from III, IV or V main group or transition group, n is an integer from 1 to 3, and m is an integer from 4 to 6 (DE-A-4 445 266). They may be present in the polymerizable preparations in a concentration of from 3 to 85% by weight, preferably from 5 to 85% by weight, and in particular from 30 to 85% by weight, based on the total mass.

For the purpose of improved incorporation into the polymer matrix it may be of advantage to hydrophobicize the abovementioned fillers by conventional techniques. Customary hydrophobicizing agents are silanes, an example being trimethoxyglycidylsilane. The average particle size of the inorganic fillers is preferably <20 µm, in particular <12 µm. Very particular preference is given to using fillers having an average particle size <7 µm.

Additionally christobalite, calcium silicate, zirconium silicate, montmorillonte, such as bentonites, zeolites, including the molecular sieves, such as sodium aluminum silicate, metal oxide powders, such as aluminum or zinc oxides and their mixed oxides, barium sulfate, calcium carbonate, gypsum, and polymer powders, are suitable as fillers.

Possible initiators according to component (d) of the preparations of the invention are: Lewis or Broensted acids or compounds which release those acids which initiate the polymerization, examples being $BF_3$ or its ethereal adducts ($BF_3$.THF, $BF_3$.$Et_2O$, etc.), $AlCl_3$, $FeCl_3$, $HPF_6$, $HAsF_6$, $HSbF_6$, $HBF_4$ or substances which initiate polymerization on exposure to UV, visible light, heat and/or pressure, such as (eta-6-cumene)(eta-5-cyclopentadienyl)iron hexafluorophosphate, (eta-6-cumene)(eta-5-cyclopentadienyl)iron tetrafluoroborate, (eta-6-cumene)(eta-5-cyclopentadienyl)iron hexafluoroantimonate, substituted diaryliodonium salts and triarylsulfonium salts, for example. As accelerators it is possible to use peroxy compounds of perester, diacyl peroxide, peroxydicarbonate, and hydroperoxide type. Preference is given to using hydroperoxides and particular preference is given to the use, as accelerator, of cumene hydroperoxide in from approximately 70 to 90% strength solution in cumene. The ratio of photoinitiator to cumene hydroperoxide can be varied within wide limits from 1:0.001 to 1:10, although preference is given to using a ratio from 1:0.1 to 1:6 and, with particular preference, from 1:0.5 to 1:4. The use of complexing agents, such as oxalic acid, 8-hydroxyquinoline, ethylenediaminetetraacetic acid, and aromatic polyhydroxy compounds, for example, is likewise possible.

It is also possible to use initiator systems composed of different components, as described in EP 0 897 710 A2, WO 98/47046 or WO 98/47047. It is preferred to use initiator systems composed of 1,2-diketones, such as camphorquinone, iodonium salts with anions causing little coordination, such as tolylcumyliodonium tetrakis (pentafluorophenyl)borate, and aromatic tertiary amines, 2-butoxyethyl-4-(dimethylamino)benzoate or ethyl 4-(dimethylamino)benzoate.

Retardants which can be added include bases, typically tertiary amines. Component (d) is present in the preparations of the invention in an amount of from 0.01 to 25% by weight, preferably from 0.01 to 20% by weight, based on the total weight of the preparation.

Suitable auxiliaries according to component (e) may be, for example, stabilizers commonly used in the dental field (e.g., Tinuvins from Ciba), pigments or diluents, for example.

Surprisingly it has been found that the silicon-containing epoxides or mixtures of component (a) of the preparations of the invention combine an advantageously low viscosity with better toxicity data than similar low-viscosity epoxides in dental compositions already described. The improved toxicity is manifested, for example, in a lower mutagenicity. Polymerizable compositions of epoxides or mixtures of epoxides of component (a) which have at least one silicon atom in the radical D of the molecules unexpectedly display a lower mutagenicity than comparable epoxides without a silicon atom in the radical D of the molecules. Comparative experiments show that the silicon-containing epoxides of the claimed preparations give better results in the mutagenicity test (Ames test, ISO/FDIS 7405) than, for example, the prior art 3,4-epoxycyclohexylmethyl 3,4-epoxycyclohexanecarboxylate.

| IUPAC designation | Ames test (ISO/FDIS 7405) |
|---|---|
| methylbis[2-(7-oxabicyclo[4.1.0]hept-3-yl)ethyl]phenylsilane | negative |
| dimethylbis[2-(7-oxabicyclo-[4.1.0]hept-3-yl)methyl] silane | negative |
| Epoxycyclohexylmethyl 3,4-epoxycyclohexanecarboxylate (control) | positive |

The epoxide-containing polymerizable preparations of the invention are particularly suitable as materials for dental purposes: for example, for producing false teeth or temporary dentition, as coating materials, for the adhesive bonding of substrates, and as dental filling materials. In this context the coating of plastics, glass, paper, films, metals or mineral substrates, for example, is possible. It is also possible, for example, to bond plastics, glass, paper, films, metals or mineral substrates. Bonding may be carried out cold, hot, or by irradiation or chemical initiation.

The polymerizable preparation may be provided in the form of a one-component system. Formulation as a two-component or multicomponent system is likewise conceivable. In that case one or more base pastes (A) may comprise epoxides or mixtures of epoxides of components (a) and (b), a portion or the entire fraction of the fillers of component (c), optionally retardants and/or accelerators as per component (d), and optionally auxiliaries of component (e). Spatially separate therefrom, one or more catalyst pastes (B) may comprise one or more initiators per component (d), optionally retardants and/or accelerators as per component (d), optionally a portion of the fillers of component (c) and optionally auxiliaries as per component (e). To give the polymerizable preparation, the pastes (A) and (B) are then reacted with one another. This is done, for example, by automatic or manual mixing of base pastes and catalyst pastes.

The preparation of the invention may be packaged in a variety of containers. Suitable examples include cartridges with one or more chambers, mixing capsules, screw-top tubes or other tubes. The polymerizable preparation may further be contained in different delivery devices.

The table below gives examples of monomer compositions which achieve the object of the present invention. The flexural strength and the water absorption were determined in accordance with ISO 4049. The volume shrinkage was calculated form the densities, determined in accordance with the principle of Archimedes, and volumes of the unpolymerized and polymerized preparations.

The monomers and monomer mixtures of component (a) all had a a viscosity of less than 3 Pas. The viscosity was determined under force control and the epoxides or epoxide mixtures of component (a) were recognized in the measuring range of 5–500 Pa as Newtonian fluids. Under these measuring conditions, with comparable toxicity and mutagenicity, the prior art monomers and monomer mixtures have viscosities of more than 20 Pas.

| Fractions in % by weight | Monomer composition 1 | Monomer composition 2 | Monomer composition 3 | Monomer composition 4 | Monomer composition 5 | Monomer composition 6 |
|---|---|---|---|---|---|---|
| Silane, methylbis[2-(7-oxabicyclo-[4.1.0]hept-3-yl)ethyl]phenyl | 60 | 40 | | | | 100 |
| Silane, 1,4-phenylenebis[dimethyl[2-(7-oxabicyclo[4.1.0]hept-3-yl)ethyl]] | 40 | | 33 | | 30 | |
| Silane, dimethylbis[2-(7-oxabicyclo-[4.1.0]hept-3-yl)methyl] | | | 33 | 50 | | |
| Disiloxane, 1,1',1''-(1,2,4-cyclohexane-triyltri-2,1-ethanediyl)tris[1,1,3,3-tetramethyl-3-[2-(7-oxabicyclo[4.1.0]-hept-3-yl)ethyl] | | | | | 40 | |
| 1,3,5,7-Tetrakis(2,1-ethanediyl-3,4-epoxycyclohexyl)-1,3,5,7-tetramethyl-cyclotetrasiloxane | | 60 | 34 | 50 | 30 | |

| Compositions of the invention with initiators and fillers, and their flexural strength, water absorption, and volume shrinkage | | | | | | | | |
|---|---|---|---|---|---|---|---|---|
| Fractions in % by weight | Example 1 | Example 2 | Example 3 | Example 4 | Example 5 | Example 6 | Example 7 | Example 8 |
| Monomer composition 1 | 36.0 | | | | | | | |
| Monomer composition 2 | | 18.0 | 23.3 | | | | | |
| Monomer composition 3 | | | | 20.5 | | | | |
| Monomer composition 4 | | | | | 19.0 | 41.0 | | |
| Monomer composition 5 | | | | | | | 20.4 | |
| Monomer composition 6 | | | | | | | | 20.0 |
| Tolylcumyliodonium tetrakis-(pentafluorophenyl)borate | 2.1 | 2.0 | 2.2 | 2.1 | 2.1 | 2.4 | 2.1 | 2.2 |
| 2-Butoxyethyl 4-(dimethylamiono)benzoate | 0.3 | 0.2 | 0.2 | 0.2 | 0.2 | 0.3 | 0.2 | 0.3 |
| Camphorquinone | 0.6 | 0.5 | 0.6 | 0.5 | 0.6 | 0.7 | 0.5 | 0.6 |
| Quartz | | 79.3 | | | 78.1 | | | |
| Schott glass GM 27884 | 61.0 | | 73.7 | 76.66 | | 55.6 | 76.8 | 76.9 |
| Tinuvin P | | | | 0.04 | | | | |
| Flexural strength (ISO4049) [MPa] | 89 | 121 | 116 | 102 | 118 | 93 | 97 | 108 |
| Water absorption [μg/mm³] | 10.8 | 6.3 | 8.1 | 7.8 | 7.6 | 19.1 | 7.7 | 6.4 |
| Volume shrinkage [% by vol.] | 1.7 | 1.1 | 1.4 | 1.2 | 1.0 | 1.9 | 1.4 | 1.4 |

What is claimed is:
1. A polymerizable dental composition comprising:
(a) from 3 to 80% by weight of an epoxide or of a mixture of epoxides corresponding to formula I:

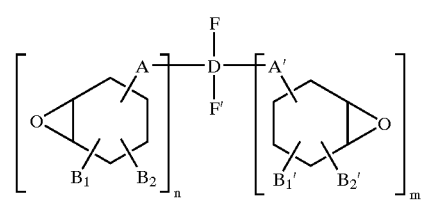

where
A and A' independently of one another are optional or represent an unbranched or branched aliphatic, cycloaliphatic or aromatic radical having from 1 to 13 carbon atoms or a combination of these radicals, wherein one or more carbon atoms could be replaced by C=O, O(C=O), Si, N or S, B1, B1', B2 and B2' independently of one another are H, an unbranched or branched aliphatic, cycloaliphatic or aromatic radical having from 1 to 6 carbon atoms or a combination of these radicals, wherein one or more carbon atoms could be replaced by O, (C=O), O(C=O), Si, N or S, F and F' independently of one another are optional or represent an unbranched or branched aliphatic, clycloaliphatic or aromatic radical having from 1 to 10 carbons or a combination of these radicals, wherein one or more carbon atoms could be replaced by (C=O), O(C=O), Si, N, or S, D comprises one of the following constituents, which is attached by way of the silicon atom to one or both of A and A':
i. Si
ii. SiG
iii. SiGG'

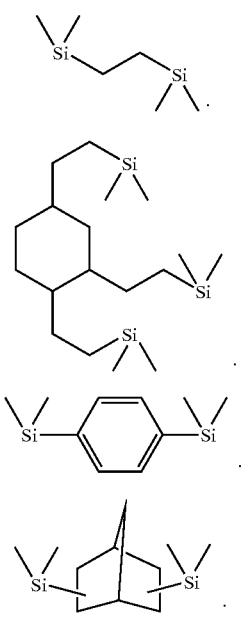

iv v vi vii

G and G' independently of one another are H, an unbranched or branched aliphatic, cycloaliphatic or aromatic radical having from 1 to 8 carbon atoms or a combination of these radicals, wherein one or more carbon atoms could be replaced by (C=O), O(C=O), Si, N or S, n and m independently of one another are 0, 1,2 or 3 and n+m gives from 2 to 4 and the molecular weight of the epoxide or the average molecular weight of the mixture of epoxides is from 250 to 1000 g/mol, (b) from 0 to 80% by weight of an epoxide or of a mixture of epoxides which are different than (a), (c) from 3 to 85% by weight of fillers, (d) from 0.01 to 25% by weight of initiators, retardants or accelerators, (e) from 0 to 25% by weight of auxiliaries, the percentages in each case being based on the total weight of the preparation.

2. The polymerizable dental composition of claim 1 comprising:

(a) from 5 to 50% by weight of an epoxide or of a mixture of epoxides corresponding to formula I where A and A' independently of one another are optional or represent unbranched or branched aliphatic, cycloaliphatic or aromatic radical having from 1 to 10 carbon atoms or a combination of these radicals, wherein one or more carbon atoms could be replaced by C=O, O(C=O) or Si, B1, B1', B2 and B2' independently of one another are H, an unbranched or branched aliphatic, cycloaliphatic or aromatic radical having from 1 to 4 carbon atoms or a combination of these radicals, wherein one or more carbon atoms could be replaced by O, (C=O), O(C=O) or Si, F and F' independently of one another are optional or represent an unbranched or branched aliphatic, clycloaliphatic or aromatic radical having from 1 to 10 carbons or a combination of these radicals, wherein one or more carbon atoms could be replaced by (C=O), O(C=O) or Si, G and G' independently of one another are H, an unbranched or branched aliphatic, cycloaliphatic or aromatic radical having from 1 to 8 carbon atoms or a combination of these radicals, wherein one or more carbon atoms could be replaced by (C=O), O(C=O), or Si, (b) from 0 to 60% by weight of an epoxide or of a mixture of epoxides which are different than (a), (c) from 15 to 85% by weight of fillers, and (d) from 0.01 to 20% by weight of initiators, retardants or accelerators.

3. The polymerizable dental composition of one of claims 1 or 2, comprising as fillers according to component (c) quartz, ground glasses, silica gels and/or silicas, granules thereof and/or ground plastics.

4. The polymerizable dental composition of one of claims 1 or 2, comprising as initiators Lewis acids and/or Broensted acids or compounds from which such acids are formed on exposure to UV light, visible light, pressure and/or heat or by chemical reaction.

5. The polymerizable dental composition of claims 1 or 2, comprising as auxiliaries diluents, stabilizers, inhibitors and/or pigments.

6. The polymerizable dental composition of one of claims 1 or 2, comprising

A at least one base paste comprising epoxides or mixtures of epoxides of components (a) and (b), a portion or the entire fraction of the fillers of component (c), optionally retardants and/or accelerators as per component (d), and optionally auxiliaries of component (e), and, spatially separate therefrom, B at least one catalyst paste comprising at least one initiator as per component (d), optionally a portion of the fillers of components (c), and optionally auxiliaries as per component (e), base paste and catalyst paste being reacted with one another to give the polymerizable dental composition.

7. A container functional as packaging comprising a receptacle containing the polymerizable dental composition of one of claims 1 or 2.

8. A container as claimed in claim 7 in the form of a cartridge.

9. A container as claimed in claim 7 in the form of a mixing capsule.

10. A delivery device comprising a delivery apparatus containing the polymerizable dental composition of one of claims 1 or 2.

11. A method of adhesively bonding substrates comprising applying the polymerizable dental composition of one of claims 1 or 2 to said substrates, and curing the composition.

12. The polymerizable dental composition of claim 1 or 2, comprising as component (a) one or more of the following epoxides:

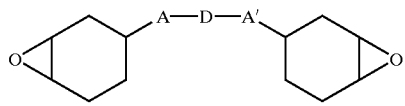

where

A and A' independently of one another are optional or represent an aliphatic radical having from 1 to 2 carbon atoms, G and G' independently of one another are H, an unbranched or branched aliphatic, cycloliphatic or aromatic radical having from 1 to 8 carbon atoms or a combination of these radicals, and the molecular weight of the epoxide or the average molecular weight of the mixture of epoxides is from 250 to 500 g/mol.

13. The polymerizable dental composition of claim 1 or 2, comprising as component (a) one or more of the following epoxides:

a) methylbis[2-(7-oxabicyclo[4.1.0]hept-3-yl)ethyl]phenyl-silane,

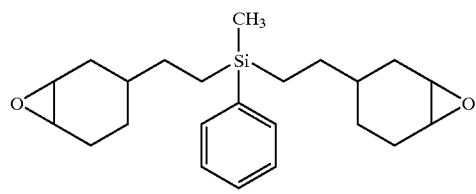

b) methylbis[2-(7-oxabicyclo[4.1.0]hept-3-yl)methyl]-silane

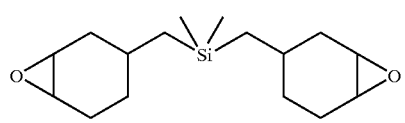

c) methylbis[2-(7-oxabicyclo[4.1.0]hept-3-yl)methyl][2-(7-oxabicyclo[4.1.0]hept-3-yl)ethyl]-silane

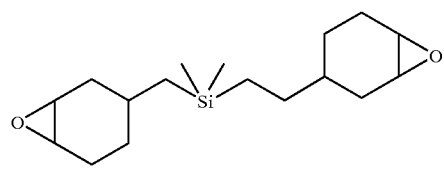

d) 1,4-phenylenebis[dimethyl[2-(7-oxabicyclo[4.1.0]hept-3-yl)ethyl]-silane

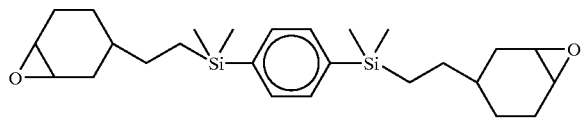

e) 1,2-ethylenbis[dimethyl[2-(7-oxabicyclo[4.1.0]hept-3-yl)ethyl]]-silane

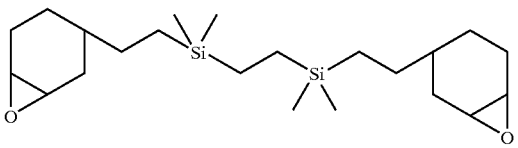

f) dimethylbis[2-(7-oxabicyclo[4.1.0]hept-3-yl)ethyl]-silane

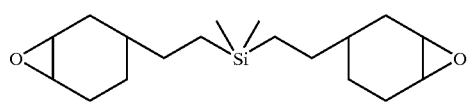

g) 2.5-bicyclo[2.2.1.]heptylenebis[dimethyl[2-(7-oxabicyclo[4.1.0]hept-3-yl)ethyl]-silane

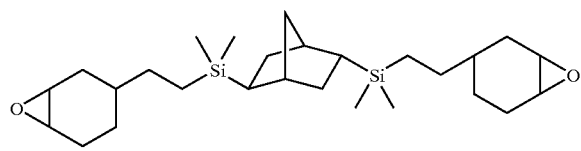

h) 1,6-hexylenebis[dimethyl[2-(7-oxabicyclo[4.1.0]hept-3-yl)ethyl]]-silane or

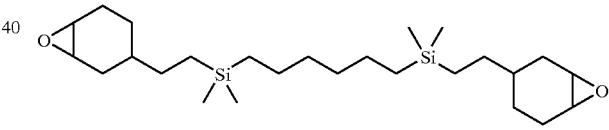

i) 1,1',1"-(1,2,4-cyclohexanetriyltri-2,1-ethanediyl)tris[dimethyl-[2-(7-oxabicyclo[4.1.0]hept-3-yl)ethyl]]-silane.

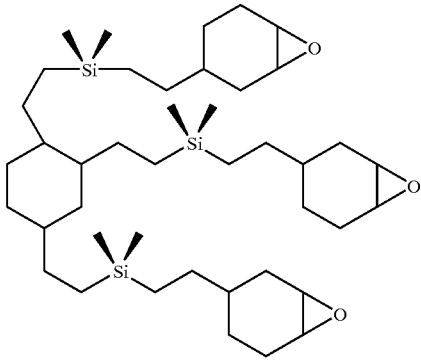

14. The polymerizable dental composition of claim 1, comprising as component (a) one or more of the following epoxides:

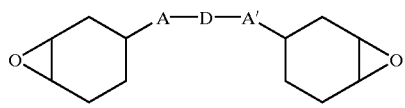

where

A and A' independently of one another are optional or represent an aliphatic radical having from 1 to 2 carbon atoms, G and G' independently of one another are H, an unbranched or branched aliphatic, cycloaliphatic or aromatic radical having from 1 to 8 carbon atoms or a combination of these radicals, wherein one or more carbon atoms could be replaced by (C=O), O(C=O), or Si, and the molecular weight of the epoxide or the average molecular weight of the mixture of epoxides is from 250 to 600 g/mol.

* * * * *

UNITED STATES PATENT AND TRADEMARK OFFICE
CERTIFICATE OF CORRECTION

PATENT NO. : 6,779,656 B2  
DATED : August 24, 2004  
INVENTOR(S) : Klettke, Thomas et al.

It is certified that error appears in the above-identified patent and that said Letters Patent is hereby corrected as shown below:

Column 5,
Line 1, after "are" insert -- H, --.
Line 3, delete "theses" and insert -- these --, therefor.
Line 26, after "aliphatic" insert -- or aromatic --.

Column 11,
Line 36, delete "dimethylamiono" and insert -- dimethylamino --, therefor.

Column 13,
Lines 8-9, delete "clycloaliphatic" and insert -- cycloaliphatic --, therefor.
Line 38, insert -- or -- before "vii".

Column 14,
Lines 15-16, delete "clycloaliphatic" and insert -- cycloaliphatic --, therefor.

Column 15,
Line 21, below "atoms," insert -- D is SiGG' --.
Line 23, delete "cycloliphatic" and insert -- cycloaliphatic --, therefor.
Line 45, delete "methylbis" and insert -- dimethylbis --, therefor.
Line 55, delete "methylbis" and insert -- dimethyl --, therefor.

Column 16,
Line 26, delete "2.5" and insert -- 2,5 --, therefor.
Line 37, after "silane" insert -- , --.

Signed and Sealed this

Twenty-third Day of August, 2005

JON W. DUDAS  
*Director of the United States Patent and Trademark Office*